United States Patent [19]

Dumoulin et al.

[11] Patent Number: 5,694,142

[45] Date of Patent: Dec. 2, 1997

[54] INTERACTIVE DIGITAL ARROW (D'ARROW) THREE-DIMENSIONAL (3D) POINTING

[75] Inventors: Charles Lucian Dumoulin, Ballston Lake; Robert David Darrow, Scotia; William John Adams, Clifton Park, all of N.Y.

[73] Assignee: General Electric Company, Schenectady, N.Y.

[21] Appl. No.: 340,783

[22] Filed: Nov. 17, 1994

Related U.S. Application Data

[63] Continuation-in-part of Ser. No. 78,335, Jun. 21, 1993.

[51] Int. Cl.$^6$ ............................................ G09G 5/00
[52] U.S. Cl. .................... 345/9; 345/156; 348/77; 353/28; 364/413.13
[58] Field of Search ................... 128/653.1, 653.2; 364/413.13, 413.22; 178/18; 345/7–9, 113, 114, 115, 133, 156, 157, 158, 167; 353/28; 348/51–53, 65, 77; 395/119, 124, 125, 127, 128; 382/128, 131, 132; 359/65; 235/1 R

[56] References Cited

U.S. PATENT DOCUMENTS

| | | | |
|---|---|---|---|
| 4,232,334 | 11/1980 | Dyson | 345/133 |
| 4,605,294 | 8/1986 | Bourdier et al. | 353/28 |
| 4,823,285 | 4/1989 | Blancato | 348/77 |
| 4,994,794 | 2/1991 | Price et al. | 345/7 |
| 5,019,976 | 5/1991 | Chiu et al. | 345/115 |
| 5,025,314 | 6/1991 | Tang et al. | 178/18 |
| 5,142,275 | 8/1992 | Rockel | 345/167 |
| 5,229,935 | 7/1993 | Yamagishi et al. | 395/128 |
| 5,252,950 | 10/1993 | Saunders et al. | 345/9 |
| 5,367,614 | 11/1994 | Bisey | 345/156 |
| 5,368,309 | 11/1994 | Monroe et al. | 345/9 |
| 5,371,778 | 12/1994 | Yanof et al. | 395/127 |
| 5,379,369 | 1/1995 | Komma et al. | 395/119 |
| 5,491,510 | 2/1996 | Gove | 345/9 |
| 5,493,595 | 2/1996 | Schoolman | 128/653.1 |
| 5,515,079 | 5/1996 | Hauck | 345/9 |
| 5,526,812 | 6/1996 | Dumoulin et al. | 345/9 |
| 5,568,384 | 10/1996 | Robb et al. | 382/132 |
| 5,569,895 | 10/1996 | Lynch et al. | 235/1 R |

OTHER PUBLICATIONS

"3D Ultrasound Display Using Optical Tracking" by Peter H. Mills, Henry Fuchs, Dept. of Computer Science, University of North Carolina, Chapel Hill, N.C. –pp. 490–497–IEEE 1990.

"A Frameless Stereotaxic Operating Microscope for Neurosurgery" by E.M. Friets, J.W. Strohbehn, J.F. Hatch and D.W. Roberts, IEEE Transactions on Biomedical Eng., vol. 36, No. 6, Jun. 1989 pp. 608–617.

*Primary Examiner*—Steven Saras
*Attorney, Agent, or Firm*—Lawrence P. Zale; Marvin Snyder

[57] ABSTRACT

An interactive three-dimensional (3D) pointing device for selecting points within a subject employs a tracking device which determines the position of the operator, a semi-transparent screen positioned by the operator and the subject and provides this information to a model workstation. The model workstation superimposes computer graphic images of internal structures of the subject on a the semi-transparent screen through which the operator is viewing the subject. The superimposed image is derived from image data either previously generated and stored or obtained with an imaging system. The images of the internal structures are registered with the operator's view of the external structures of the operator. The operator interactively views internal and external structures and the relation between them simultaneously, while moving the screen to select 3D target points at an image depth within the subject. Optionally other input devices may be used to identify current 'target points' as selected points. The 3D points are then provided to an output device which utilizes them. Another embodiment employs stereoscopic viewing methods to provide 3D representations of the internal images superimposed on external structures to allow the operator to employ parallax to select 3D points.

13 Claims, 3 Drawing Sheets

1

INTERACTIVE DIGITAL ARROW (D'ARROW) THREE-DIMENSIONAL (3D) POINTING

CROSS REFERENCE TO RELATED APPLICATIONS

This is a continuation-in-part (continuation in part) of "A Display System For Enhancing Visualization Of Body Structures During Medical Procedures" by C. L. Dumoulin, R. D. Darrow, W. J. Adams, Ser. No. 08/078,335, filed Jun. 21, 1993. This application is related to U.S. patent applications "A Display System For Enhancing Visualization Of Body Structures During Medical Procedures" by C. Dumoulin, R. Darrow, W. Adams Ser. No. 08/340,784 filed Nov. 17, 1994 filed along with this application; and "Computer Graphic and Live Video System for Enhancing Visualization of Body Structures During Surgery" by Chris Nafis, Tim Kelliher, Harvey Cline, Bill Lorensen, David Altobelli, Ron Kikinis, Robert Darrow and Charles Dumoulin, Ser. No. 08/049,913 filed Apr. 20, 1993, both hereby incorporated by reference and assigned to the present assignee.

BACKGROUND OF THE INVENTION

1. Field of the Invention

The present invention relates to a system for computer graphics and more specifically to a three dimensional pointing device.

2. Description of the Prior Art

Presently, there are many known devices used in conjunction with computing equipment for the purpose of pointing and locating two-dimensional (2D) points. Examples include the computer mouse, drawing tablet and light pen. These devices employ optical or mechanical to identify 2D locations.

There are also three-dimensional (3D) locating devices which may employ electromagnetic, acoustic or infrared principles to locate 3D points.

The infrared and optical locating devices require a visual line of sight between a source and a receiver. The acoustic locating devices require sound to be received unobstructed or errors result in the computed 3D location.

These are used primarily to track points external to subjects. Due to their nature, they are not easily adaptable for locating points inside a solid subject.

If these could be modified to locate internal points of a solid subject, there is no feedback to an operator indicating the internal locations to be selected. Futhermore, the operator cannot visualize internal structures of the subject.

Currently there is a need for a device to aid an operator in non-invasively selecting locations within a solid subject.

OBJECTS OF THE INVENTION

An object of the present invention is to provide a system which aides in surgery by simultaneously superimposing an image of internal structures upon external structures even if the patient changes position or if the operator changes his viewing angles.

Another object of the present invention is to provide an interactive system which displays desired internal structures upon external structures, correctly registered.

Another object of the present invention is to provide an operator a "heads up" display of images of internal structures superimposed upon external structures of an object.

Another object of the present invention is to provide an interactive system which allows selection of internal structures and surfaces to be superimposed upon corresponding external structures of a subject.

Another object of the present invention is to provide a pointing system which permits an operator to point to a selected location within a subject without placing a physical object within the subject.

SUMMARY OF THE INVENTION

A real-time apparatus for interactively pointing to three dimensional (3D) locations within a subject displays correctly registered images of internal and external structures of a subject on a semi-transparent screen. This allows an operator to interactively view and identify 3D locations within the subject.

A representation of internal structures of a subject are provided to a workstation. This representation may be generated and previously stored by means such as an imaging means or CAD/CAM system. An operator positions the semi-transparent screen, held by a movable arm, between the operator and the subject such that the operator views external structures of the subject through the semi-transparent screen. Three-dimensional positions and orientations of the subject, semi-transparent screen and operator are monitored by a tracking device in real-time and fed to the workstation. The workstation receives the positions and orientation from the tracking device and creates an image of internal structures corresponding to the viewing angle of the operator. This image is superimposed upon the view of the external structures of the subject such that the internal and external structures are correctly registered.

In one embodiment the semi-transparent screen may have an identification, such as cross-hairs, on the screen, and be initialized with a predetermined image depth from the screen, such that a 3D point, a 'target point', is defined being the image depth along a line of sight from the center of the cross hairs. This 'target point' is selected by the operator physically moving either himself, the subject, or the screen. The view also changes such that the operator may 'look into' the subject to identify target points. These target points may be interactively provided to other output equipment as 3D coordinates. An input device may also be employed which, when activated, identifies the current 'target point' identified by the cross hairs and image depth, as a selected point.

In an alternative embodiment, a two dimensional (2D) pointing device is employed along with the screen position and orientation to define 3D target points. One such preferred 2D input device employs touch sensors on the screen to identify the 2D location touched by the operator. This 2D location along with the position and orientation of the screen results in a 3D location.

Each of the above embodiments may also be employed in a stereo version which provides depth perception.

BRIEF DESCRIPTION OF THE DRAWINGS

The features of the invention believed to be novel are set forth with particularity in the appended claims. The invention itself, however, both as to organization and method of operation, together with further objects and advantages thereof, may best be understood by reference to the following description taken in conjunction with the accompanying drawings in which:

DETAILED DESCRIPTION OF THE INVENTION

Figure 1:
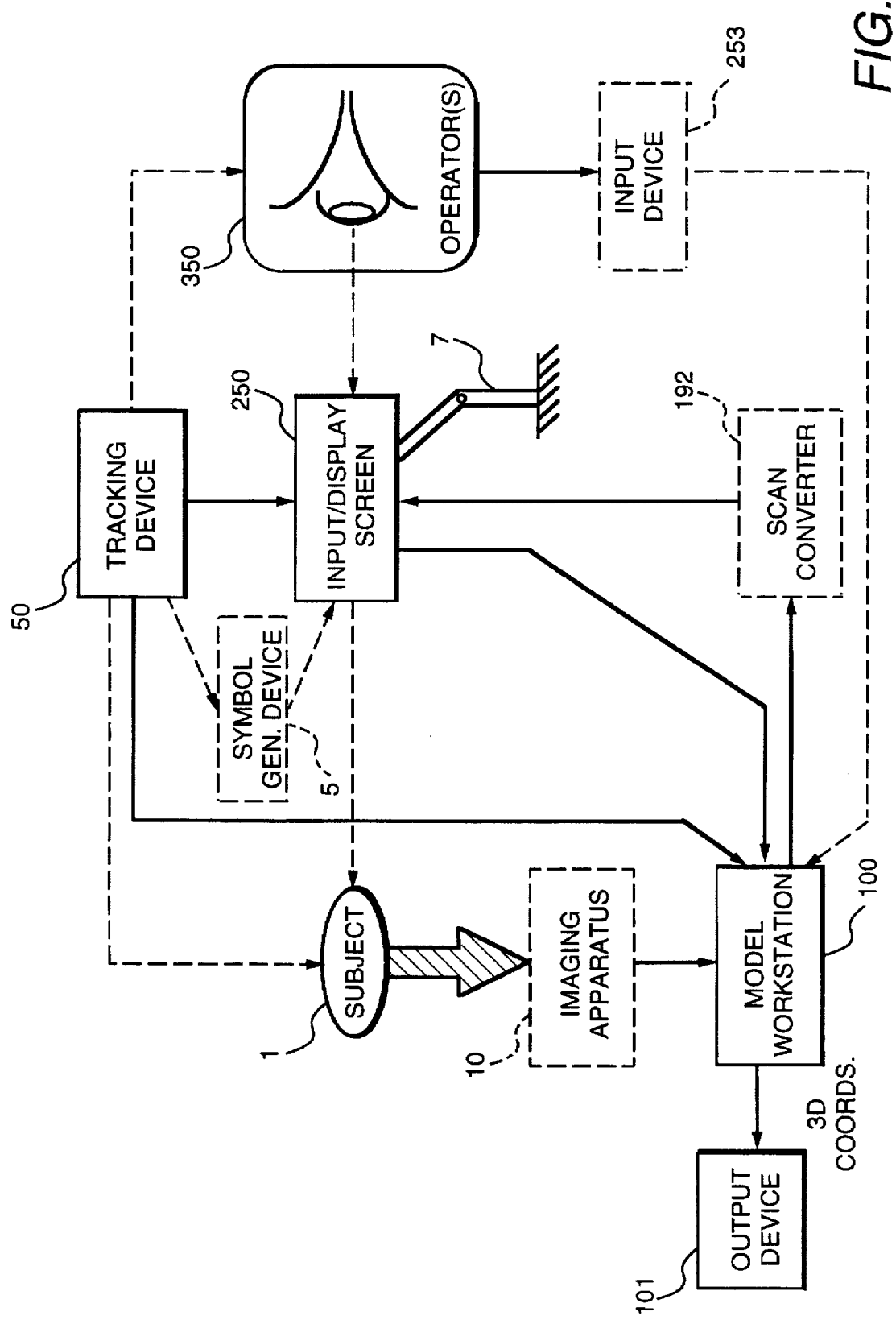
FIG. 1 is a simplified block diagram of a first embodiment of an interactive 3D pointing device according to the present invention.

In FIG. 1, a representation of internal structures of a subject 1 are provide to a model workstation 100. The representation may be a computer model generated by a computer aided design/computer aided manufacturing system, or may be acquired by scanning subject 1 with an imaging apparatus 10 such as a magnetic resonance (MR) imaging apparatus, a computed axial tomography (CAT) apparatus, a positron emission tomography (PET) or similar imaging device capable of creating multi-dimensional volumetric data such as 3-dimensional (3-D) data, from internal structures of the subject. After imaging, apparatus 10 provides the volumetric data to a model workstation 100. Once the volumetric data has been provided to model workstation 100, imaging apparatus 10 is no longer required. This is important since some procedures need not be performed with the subject situated within the confines of an imaging apparatus, which can be constricting in the case of MR imaging. In alternative embodiments, imaging apparatus 10 may be interactively employed during the procedure. Model workstation 100 stores the volumetric data and creates computer generated models from the data capable of being scaled, rotated and otherwise manipulated, without the further need for imaging apparatus 10.

A semi-transparent screen 250 is held by moveable arm 7 which allows an operator 350 to interactively position semi-transparent screen 250 between subject 1 and operator 350. The semi-transparent screen may be constructed with a surface material which may be written upon and erased.

A tracking device 50 monitors the location and orientation of operator 350, semi-transparent screen 250 and subject 1.

Operator 350 views the external structures of subject 1 through semi-transparent screen 250 as he moves semi-transparent screen 250. Tracking device 50 provides the locations and orientations to model workstation 100 which produces an image of internal structures which corresponds to the operator's view of external structures, and both internal and external structures are 'registered'. Conventional methods of computer model rendering and display may be employed provided the geometry and scaling are performed to render the internal structures properly registered with the external structures. If a screen depth distance is preselected, and a location on the screen is also preselected, a 3D 'target point' may be identified being the screen location projected the screen depth away from semi-transparent screen 250. The screen location may be identified by cross hairs or other on the screen. By tilting and moving semi-transparent screen 250, operator 350 may position the 'target point' at any position within subject 1. As operator moves semi-transparent screen closer to the subject, the imaging plane gets deeper into the subject; and as the operator 350 move the screen closer to him, the imaging plane moves closer to the operator. The view of internal structures created by model workstation 100 which operator 350 sees is related to the position/orientation of the screen and the screen depth. The operator therefore may look into the subject and choose a three dimensional point. Model workstation 100 has all of the information necessary to compute the geometry and convert the 'target points' into 3D locations. These 3D location are then provided to an output device 101 which utilizes them. Output device 101 may be any device which requires 3D locations defined within a solid object.

The signal from model workstation 100 may be converted from a computer monitor signal, such as an RGB computer monitor signal, to a video format by passing it through a scan converter 192 (shown in phantom), depending on the display format required by semi-transparent screen 250.

The invention may further include an input device 253, which allows operator 350 to select the current 'target point' as a selected point, or allow operator 350 to select a number of 3D points by moving the screen as the input device is activated to 'drag' the 'target point' through a 3D trajectory. A number of endpoints may be selected and connected in conventionally known fashions to define lines, curves, shapes and volumes.

Another element which will add to the systems usefulness would be to employ a symbol generator 5 coupled to the tracking device to receive the location/position information and therefore determines the location of the 'target point'. It then displays a symbol on semi-transparent screen 250 indicating the position of the 'target point' in relation to both internal and external structures of subject 1. The 'target point' information may also be received from other elements which know this location.

Figure 2:
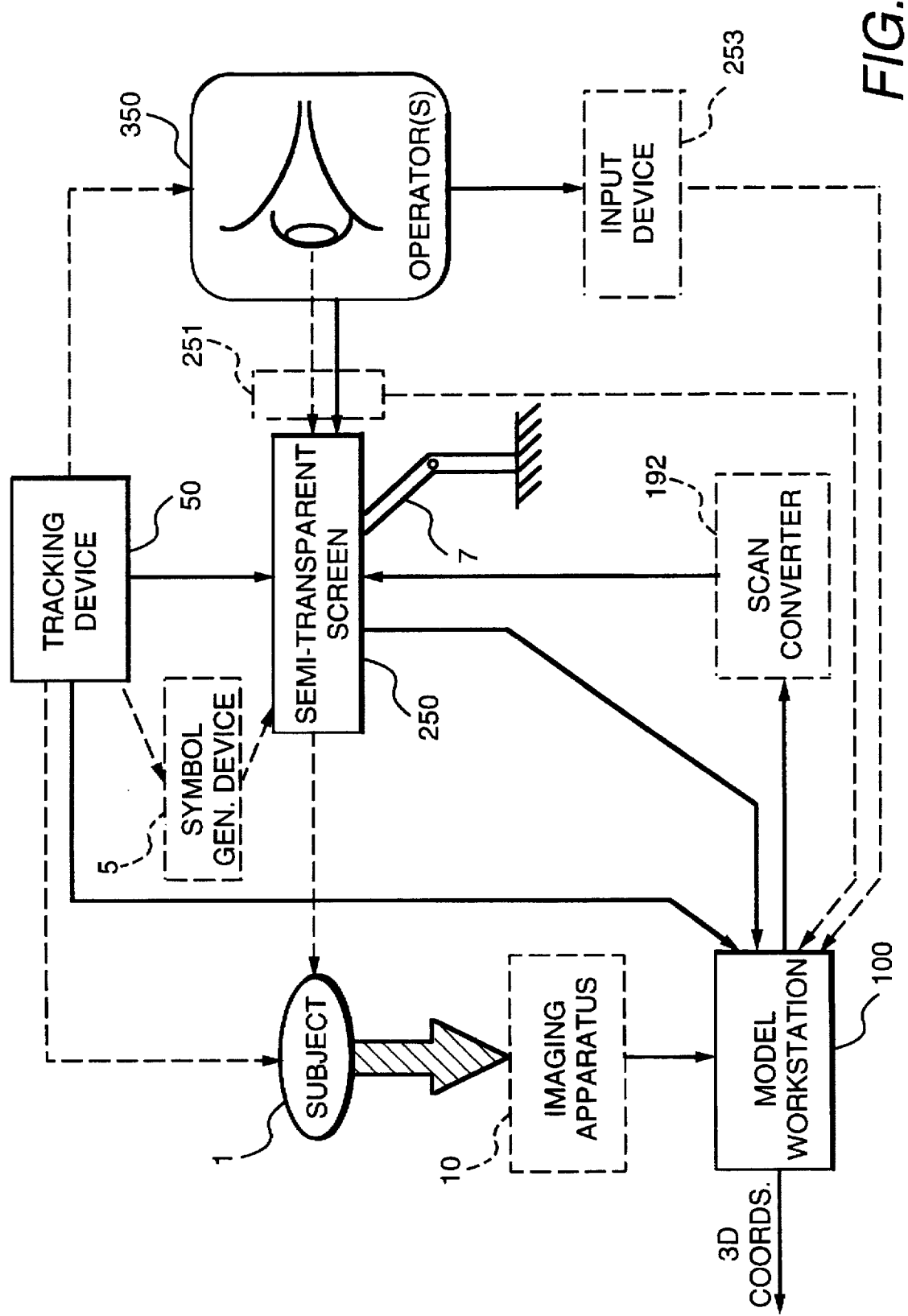
FIG. 2 is a simplified block diagram of a second embodiment of an interactive 3D pointing device according to the present invention.

In FIG. 2 a simplified block diagram illustrates a second embodiment of the present invention. Blocks having the same name and number function as described in the previous embodiment.

In this embodiment the screen location is selectable. The first embodiment employed a fixed screen location which was marked on the screen. In the second embodiment, an input device 251 is employed to allow operator 350 to interactively select a screen location, which when combined with a screen depth, determines the 'target point'. Touch sensors are preferred for input device 251 to determine a screen location touched by operator 350.

The screen depth may be fixed, as in the first embodiment, or be initialized through input device, such as input device 251. The screen depth may be provided to the system through input device 251.

As before, the operator may select 3D locations and 'drag' through a trajectory by touching the screen, and keeping his finger in contact with the screen as he moves the screen.

As set forth in the previous embodiment, optionally a symbol generation device 5 and input device 253 may be added which function as described above.

This effectively provides a 3D interface which is a very logical method of allowing the operator to search through a volume of the subject by moving the imaging plane throughout an area of interest.

The degree of transparency of internal images to external images, or any of various other special effects, may again be selected by an appropriate input device.

Operator 350 may interactive select points within subject 1, even if subject 1 moves since the subject operator and semi-transparent screen are tracked and the image created is based upon the tracked positions and orientations.

Figure 3:
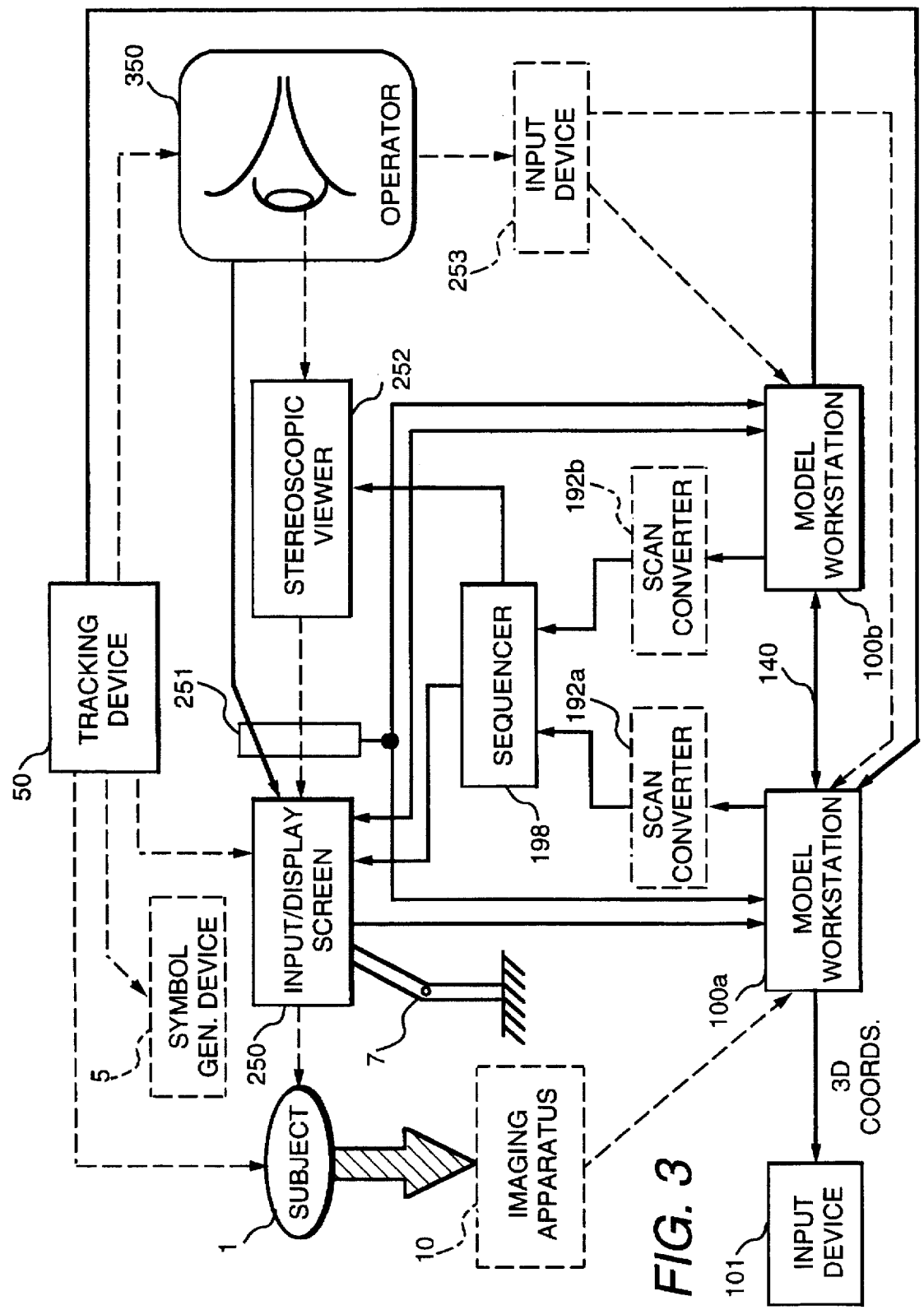
FIG. 3 is a simplified block diagram of yet a third embodiment of an interactive 3D pointing device according to the present invention.

FIG. 3 illustrates another embodiment of the present invention in which operator 350 receives a stereoscopic view of internal and external structures of subject 1. Each of the eyes of operator 350 differs in its orientation with relation to the subject therefore a different view is provided to each eye. Tracking device 50 tracks the relative location $(x_1,y_1,z_1)$ and orientation angle $(\alpha_1, \phi_1, \theta_1)$ between a first eye of operator 350 and subject 1. Tracking device 50 also tracks a second location $(x_2,y_2,z_2)$ and orientation $(\alpha_2, \phi_2, \theta_2)$ between a second eye of operator 350 and subject 1. The second location and orientation can be measured independently by tracking device 50; or the location and orientation of the first eye can be used to compute the location and orientation of the second eye. The locations and orientations are fed to a first model workstation 100a, and a second model workstation 100b which create a right and left computer graphic image at locations $(x_1,y_1,z_1)$, $(x_2,y_2,z_2)$, respectively, and orientations $(\alpha_1, \phi_1, \theta_1)$ $(\alpha_2, \phi_2, \theta_2)$ respectively, corresponding to the views of each eye of operator 350, respectively.

The left and right computer generated image, pertaining to a left and right view, respectively, are converted to video format if required by scan converters 192a, 192b (shown in phantom) which pass the converted computer generated signals to a sequencer 198. Sequencer 198 may be a conventional video sequencer. Sequencer 198 passes the left computer generated image to semi-transparent screen 250. Sequencer 198 then passes the right computer generated image to semi-transparent screen 250. Sequencer 198 alternates many times per second, in synchronization, between right and left views.

The image displayed on semi-transparent screen 250 is time multiplexed to produce an image to the left eye and right eye of the operator in an alternating fashion. A stereoscopic viewer 252 is synchronized to a sequencer 198 and operates to block the vision of the operator's left or right eye allowing the opposite eye to view the image on semi-transparent screen 250 for an instant and vice-versa. This allows operator 350 to see the left image with the left eye while the right eye sees nothing and the right image with the right eye while the left eye sees nothing in rapid succession. This creates a stereoscopic illusion, adding the dimension of depth perception in viewing the image displayed on semi-transparent screen 250. Operator may now use parallax to interactively select 3D points within subject 1.

For all embodiments of the invention the image created by model workstation(s) must be registered (coincide) with the external structures as viewed by operator 350. Initialization may be accomplished by manual input from the operator to rotate, translate and scale the computer generated image(s) until they coincide with the scene observed through the semi-transparent screen, or by employing tracking device 50 to set initial parameters. Once the 3D model and the visual image of subject 1 are aligned, tracking device 50 keeps them registered.

In the present embodiments of the invention, semi-transparent screen 250 interposed between operator 350 and subject 1 is constructed with a liquid crystal display or it can be comprised of a partially silvered mirror reflecting an image from a video monitor. Input/display screen 250 has a relatively large dimensions approximately equal to that of the region of interest of subject 1.

While several presently preferred embodiments of the novel visualization system have been described in detail herein, many modifications and variations will now become apparent to those skilled in the art. It is, therefore, to be understood that the appended claims are intended to cover all such modifications and variations as fall within the true spirit of the invention.

What is claimed is:

1. A real-time three dimensional (3D) pointing device for identifying 3D locations within a subject comprising:

a) a semi-transparent screen interposed between said subject and an operator for displaying an image provided to it to appear superimposed on external structures of said subject seen through the screen;

b) a moveable mechanical arm for holding the semi-transparent screen in a position and orientation selected by said operator between said operator and said subject such that said operator may view said subject through said semi-transparent screen;

c) touch sensors for indicating a two dimensional (2D) position of the semi-transparent screen selected by said operator and identifying this position as a screen location;

d) a tracking device for repeatedly measuring the location and orientation of the operator, said subject, and the semi-transparent screen;

e) a symbol generation unit coupled to the tracking device for determining a depth based upon the screen distance from the subject, and for displaying a symbol at the 'target location' defined as the screen location and depth on the semi-transparent screen in proper relation to the internal and external structures; and f) a workstation coupled to the tracking device, for receiving the locations and orientations of said subject, operator and the semi-transparent screen, creating an image of internal structures of said subject from a set of imaging data on the semi-transparent screen consistent with the locations and orientations of the operator, said subject and the semi-transparent screen.

2. The real-time three dimensional (3D) pointing device of claim 1 wherein the semi-transparent screen is one capable of adjustable the relative degree of transparency of the images of the internal and external structures.

3. The real-time three dimensional (3D) pointing device of claim 1 further comprising touch sensors for indicating a two dimensional (2D) position of the semi-transparent screen selected by said operator and identifying this position as the screen location to the workstation.

4. The real-time three dimensional (3D) pointing device of claim 1 further comprising a symbol generation unit coupled to the tracking device for displaying a symbol representing the 'target location' on the semi-transparent in proper relation to the internal and external structures.

5. The real-time three dimensional (3D) pointing device of claim 1 further comprising a moveable mechanical arm for holding the semi-transparent screen in a position and orientation selected by said operator between said operator and said subject such that said operator may view said subject through said semi-transparent screen.

6. The real-time three dimensional (3D) pointing device of claim 1 further comprising an imaging device for obtaining a 3D set of imaging data of internal structures of said subject and for providing the 3D set of imaging data to the workstation.

7. The real-time three dimensional (3D) pointing device of claim 1 wherein the workstation creates stereoscopic pairs of images of internal structures, and further comprising:
   stereoscopic display means synchronized with the semi-transparent screen for providing each of the stereoscopic pairs of images to each eye of an operator thereby simulating a 3D image of internal structures superimposed upon and external structures of said subject.

8. The real-time three dimensional (3D) pointing device of claim 1 wherein the semi-transparent screen has a surface constructed of a material which may be written upon and erased.

9. A method of aiding an operator in identifying three-dimensional (3D) locations within a subject comprising the steps of:
   a) acquiring multi-dimensional imaging data defining internal structures of said subject;
   b) positioning a semi-transparent screen at the selected location and orientation between an operator and said subject allowing the operator to view external structures of said subject through the semi-transparent screen;
   c) measuring locations and orientations of said subject, said operator and the semi-transparent screen;
   d) superimposing a computer generated image of the internal structures on the semi-transparent screen consistent with the measured locations and orientations from the imaging data;
   e) determining a position of a semi-transparent screen touched by the operator;
   f) identifying this position as the selected screen location;
   g) calculating a depth within the subject being a function of the distance between the screen and subject; and
   h) creating a symbol on the screen representing a 3D 'target location', being the depth from the selected screen location.

10. The method of aiding an operator in identifying 3D locations within a subject of claim 9 further comprising, after the step of superimposing a computer generated image, the steps of:
    a) determining a position of a semi-transparent screen touched by the operator;
    b) identifying this position as the selected screen location.

11. The method of aiding an operator in identifying 3D locations within a subject of claim 9 further comprising, after the step of superimposing a computer generated image, the step of operating an input device to identify a currently 'target location' as a 'selected point'.

12. The method of aiding an operator in identifying 3D locations within a subject of claim 9 wherein steps "b" through "e" are repeated to allow the operator to interactively view internal and external structures while identifying 3D points within said subject.

13. A real-time three dimensional (3D) pointing device for interacting with an operator to select 3D locations of stored computer graphic models of structures within a subject comprising:
    a) a semi-transparent screen allowing said operator to see external structures of said subject through the screen and also for displaying images of internal structures, superimposed upon the external structures;
    b) a mechanical arm coupled to the screen and fixed at a second end for adjustably holding the semi-transparent screen between said subject and said operator in an operator-selected position;
    c) touch sensors for interactively determining 2D screen locations touched by the operator;
    d) tracking device for measuring locations and orientation of the semi-transparent screen, said operator and subject;
    e) a workstation coupled to the semi-transparent screen, the touch sensors, tracking device, for receiving the locations and orientations of the screen, said subject, and operator, for displaying computer graphic models of said internal structures of said subject correctly registered with said subject's external structures from the operator's location and position;
    f) symbol generation device coupled to the tracking device for determining a distance between the screen and said subject, determining a depth perpendicular to the screen within said subject being a function of this distance, and displaying a symbol on the screen representing a 3D location defined by the 2D screen location selected and the depth, as viewed from operator location and orientation through the screen.

* * * * *